United States Patent
Kwon et al.

(10) Patent No.: US 10,321,827 B2
(45) Date of Patent: Jun. 18, 2019

(54) DEVICES AND METHODS FOR NONINVASIVE PHYSIOLOGICAL ANALYSIS

(71) Applicant: SAMSUNG ELECTRONICS CO., LTD., Suwon-si (KR)

(72) Inventors: Yongjoo Kwon, Yongin-si (KR); Jaemin Kang, Seoul (KR); Sunkwon Kim, Suwon-si (KR); Younho Kim, Hwaseong-si (KR); Sangyun Park, Hwaseong-si (KR); Seongho Cho, Gwacheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 987 days.

(21) Appl. No.: 14/813,840

(22) Filed: Jul. 30, 2015

(65) Prior Publication Data
US 2016/0150965 A1 Jun. 2, 2016

(30) Foreign Application Priority Data
Nov. 28, 2014 (KR) .................. 10-2014-0169182

(51) Int. Cl.
*A61B 5/05* (2006.01)
*A61B 5/00* (2006.01)
*A61B 5/053* (2006.01)
*A61B 8/00* (2006.01)
*A61B 5/1172* (2016.01)
*A61B 5/1455* (2006.01)

(52) U.S. Cl.
CPC .......... *A61B 5/0077* (2013.01); *A61B 5/0059* (2013.01); *A61B 5/053* (2013.01); *A61B 5/1172* (2013.01); *A61B 5/4887* (2013.01); *A61B 8/4236* (2013.01); *A61B 8/4245* (2013.01); *A61B 5/1455* (2013.01); *A61B 5/442* (2013.01); *A61B 5/6844* (2013.01); *A61B 2562/046* (2013.01); *A61B 2576/02* (2013.01)

(58) Field of Classification Search
CPC ....... A61B 5/00; A61B 5/0077; A61B 5/0059; A61B 5/1455
See application file for complete search history.

(56) References Cited

U.S. PATENT DOCUMENTS 7,358,515 B2 4/2008 Setlak et al.
8,512,242 B2 8/2013 LeBoeuf et al.
(Continued)

FOREIGN PATENT DOCUMENTS

JP 3579686 B2 10/2004
JP 2008186125 A 8/2008
(Continued)

*Primary Examiner* — Joel F Brutus
(74) *Attorney, Agent, or Firm* — Sughrue Mion, PLLC

(57) ABSTRACT

Provided are a physiological signal analysis device and method to detect and analyze physiological information of a subject. The physiological signal analysis device includes a memory device configure to store a wrinkle pattern at a measurement position of a subject as a reference position; a sensor configured to sense the reference position and a physiological signal of the subject at the reference position in response to the stored reference position being within a range of the sensor; and a signal processor configured to process the physiological signal sensed the sensor.

16 Claims, 13 Drawing Sheets

(56) References Cited

U.S. PATENT DOCUMENTS

| | | | |
|---|---|---|---|
| 2005/0063571 A1* | 3/2005 | Setlak | G06K 9/00013 382/124 |
| 2008/0129705 A1* | 6/2008 | Kim | G06F 3/016 345/174 |
| 2008/0200790 A1* | 8/2008 | Kim | A61B 5/0507 600/365 |
| 2010/0317941 A1* | 12/2010 | Kuhn | A61B 5/1459 600/323 |
| 2012/0275669 A1* | 11/2012 | Kim | G06K 9/0002 382/124 |
| 2014/0196131 A1* | 7/2014 | Lee | G06F 21/35 726/7 |

FOREIGN PATENT DOCUMENTS

| | | |
|---|---|---|
| JP | 4662543 B2 | 3/2011 |
| KR | 1020120094590 A | 8/2012 |

* cited by examiner

DEVICES AND METHODS FOR NONINVASIVE PHYSIOLOGICAL ANALYSIS

CROSS-REFERENCE TO RELATED APPLICATION

This application claims priority from Korean Patent Application No. 10-2014-0169182, filed on Nov. 28, 2014 in the Korean Intellectual Property Office, the disclosure of which is incorporated herein in its entirety by reference.

BACKGROUND

1. Field

Apparatuses and methods consistent with exemplary embodiments relate to a physiological or biometric signal analysis device applicable to, for example, a wearable blood-pressure measuring device, a wearable blood-sugar measuring device, a wearable cholesterol measuring device, and so forth.

2. Description of the Related Art

Invasive measuring methods are widely used along with many medical devices to perform various medical examinations. Invasive measurement with respect to a human subject may include, for example, sampling blood from the subject and analyzing the sampled blood. However, the subject may experience significant pain when blood is sampled and a reagent reacting with a particular substance in the blood during blood analysis and a colorimetric assay and optical equipment have to be used.

To solve this problem, various types of physiological information detection devices have been developed. In particular, with the popularization of various wearable devices that a subject may directly wear, healthcare specialized devices have been developed.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments provide a physiological or biometric signal analysis device which includes a measurement position sensor capable of sensing a measurement position to measure a physiological or biometric signal corresponding to a consistent measurement position, so that the device may perform a consistent and accurate analysis of health information.

Further, one or more exemplary embodiments provide a method for analyzing a physiological or biometric signal according to a coherent measurement position by using a measurement position sensor.

According to an aspect of an exemplary embodiment, there is provided a physiological signal analysis device including: a memory device configure to store a wrinkle pattern at a measurement position of a subject as a reference position; a sensor configured to sense the reference position and a physiological signal of the subject at the reference position in response to the stored reference position being within a range of the sensor; and a signal processor configured to process the physiological signal sensed by the sensor.

The physiological signal analysis device may further include a display configured to display the physiological signal processed by the signal processor.

The memory device, the sensor, the signal processor, and the display may be connected to a wearable device worn by the subject, a healthcare related device, or a medical device.

The sensor may include: a measurement position sensor configured to periodically sense the reference position; and a physiological signal sensor configured to sense the physiological signal at the reference position in response to the stored reference position being within a range of the measurement position sensor.

The measurement position sensor may include a measurement position sensing pixel, and the physiological signal sensor may include a physiological signal sensing pixel.

The measurement position sensing pixel or the physiological signal sensing pixel may include at least one of: a light emitter configured to radiate light onto the subject and a light receiver configured to receive light that is emitted from the subject and carries physiological information of the subject; a capacitive electrode; an ultrasound wave generator configured to radiate an ultrasound wave to the subject; and an ultrasound wave receiver configured to measure an ultrasound wave that is emitted from the subject and carries physiological information of the subject.

The capacitive electrode may be a transparent electrode that prevents the measurement position sensing pixel and the physiological signal sensing pixel from interfering with each other.

The measurement position sensing pixel and the physiological signal sensing pixel may be separately configured on a two-dimensional plane.

The measurement position sensing pixel and the physiological signal sensing pixel may be arranged alternately on a two-dimensional plane.

The physiological signal analysis device may further include a heterogeneous signal generator configured to separately generate a measurement signal sensing signal and a physiological signal sensing signal according to heterogeneous driving signals for the measurement position sensor and the physiological signal sensor, respectively.

The measurement position sensing pixel may be configured to sense an electric-field signal and the physiological signal sensing pixel may be configured to sense an optical signal.

The measurement position sensor may include: a fingerprint recognition sensor configured to sense the reference position; and a proximity recognition sensor configured to sense a contact state with respect to the reference position.

The proximity recognition sensor may include a plurality of proximity recognition sensors.

The sensor may include a sensing pixel and a heterogeneous signal generator configured to separately generate a measurement signal sensing signal and a physiological signal sensing signal according to heterogeneous driving signals.

According to an aspect of another exemplary embodiment, there is provided a physiological signal analysis method including: setting and storing a wrinkle pattern at a measurement position of a subject as a reference position; periodically sensing the reference position; and measuring a physiological signal at the reference position in response to the stored reference position being within a range of a measurement position sensor.

The setting and storing of the wrinkle pattern at the measurement position of the subject as the reference position may include automatically setting and storing a single reference position or a plurality of reference positions.

The setting and storing of the wrinkle pattern at the measurement position of the subject as the reference position may include determining, by a proximity recognition sensor, a proximity with respect to the measurement position, and setting and storing a single reference position or a plurality of reference positions in response to the proximity recognition sensor being proximate to the measurement position.

The setting and storing of the wrinkle pattern at the measurement position of the subject as the reference position may include manually setting and storing a single reference position or a plurality of reference positions.

The setting and storing of the wrinkle pattern at the measurement position of the subject as the reference position may include manually setting and storing a single reference position or a plurality of reference positions in response to the proximity recognition sensor determining that the proximity recognition sensor is proximate to the measurement position.

According to an aspect of another exemplary embodiment, there is provided a physiological signal analysis method including: setting and storing a wrinkle pattern at a measurement position of a subject as a reference position; sensing a proximity level with respect to the subject; periodically sensing the reference position in response to the sensed proximity level being within a predetermined range; and measuring a physiological signal at the reference position in response to the stored reference position being within a range of the measurement position sensor.

BRIEF DESCRIPTION OF THE DRAWINGS

The above and/or other aspects will be more apparent and more readily appreciated from the following description of the by describing certain exemplary embodiments, with reference to the accompanying drawings, in which.

DETAILED DESCRIPTION

Figure 1:
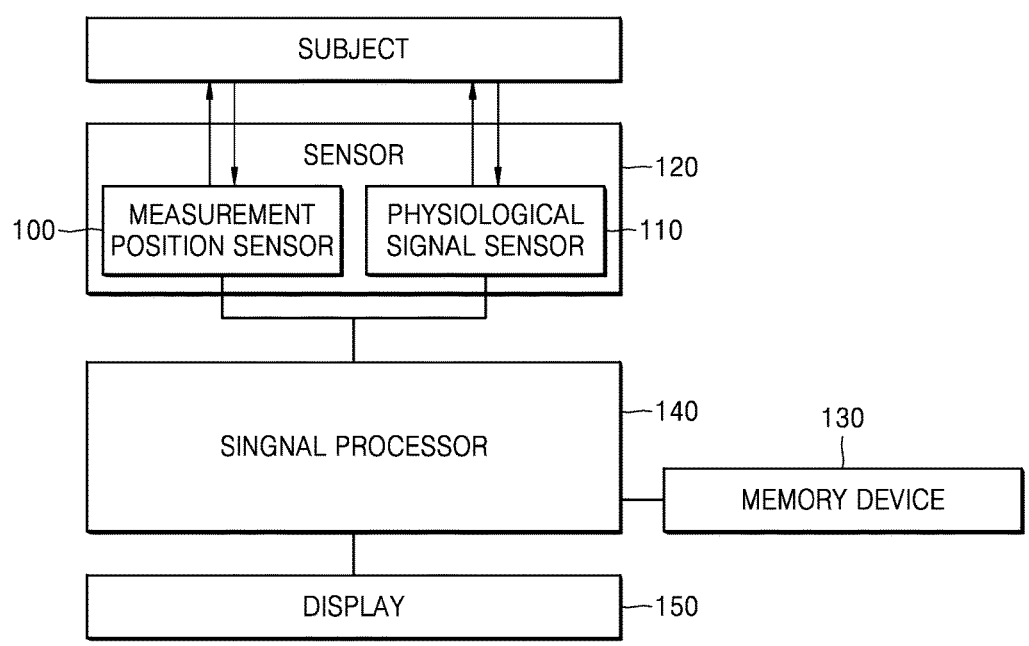
FIG. 1 illustrates a block diagram of a physiological or biometric signal analysis device according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Expressions such as "at least one of," when preceding a list of elements, modify the entire list of elements and do not modify the individual elements of the list. When a part "includes" a component, this means that the part may further include another component, rather than excluding another component, unless described otherwise.

A physiological or biometric signal analysis device senses a physiological or biometric signal at a consistent measurement position from a subject and analyzes physiological information by using the sensed physiological signal.

FIG. 1 illustrates a block diagram of a physiological or biometric signal analysis device according to an exemplary embodiment. Referring to FIG. 1, the physiological signal analysis device having a measurement position sensing function may include a sensor 120, a memory device 130, a signal processor 140, and a display 150. The sensor 120 may include a measurement position sensor 100 and a physiological signal sensor 110. The memory device 130 stores the shape of a wrinkle and/or a pattern of wrinkles at a measurement position of a subject as a reference position 101. The present embodiment is not limited thereto, and the memory device 130 may store additional micro features at the measurement position, such as scars, freckles, and moles on the skin surface of the subject. The memory device 130 may store two or more reference positions. The measurement position sensor 100 periodically senses the reference position 101, and the physiological signal sensor 110 senses a physiological signal at the reference position 101 if the stored reference position 101 enters a range of the measurement position sensor 100. The signal processor 140 processes signals of the measurement position sensor 100 and the physiological signal sensor 110, and the display 150 displays a physiological signal measured by the physiological signal sensor 110.

Figure 2:
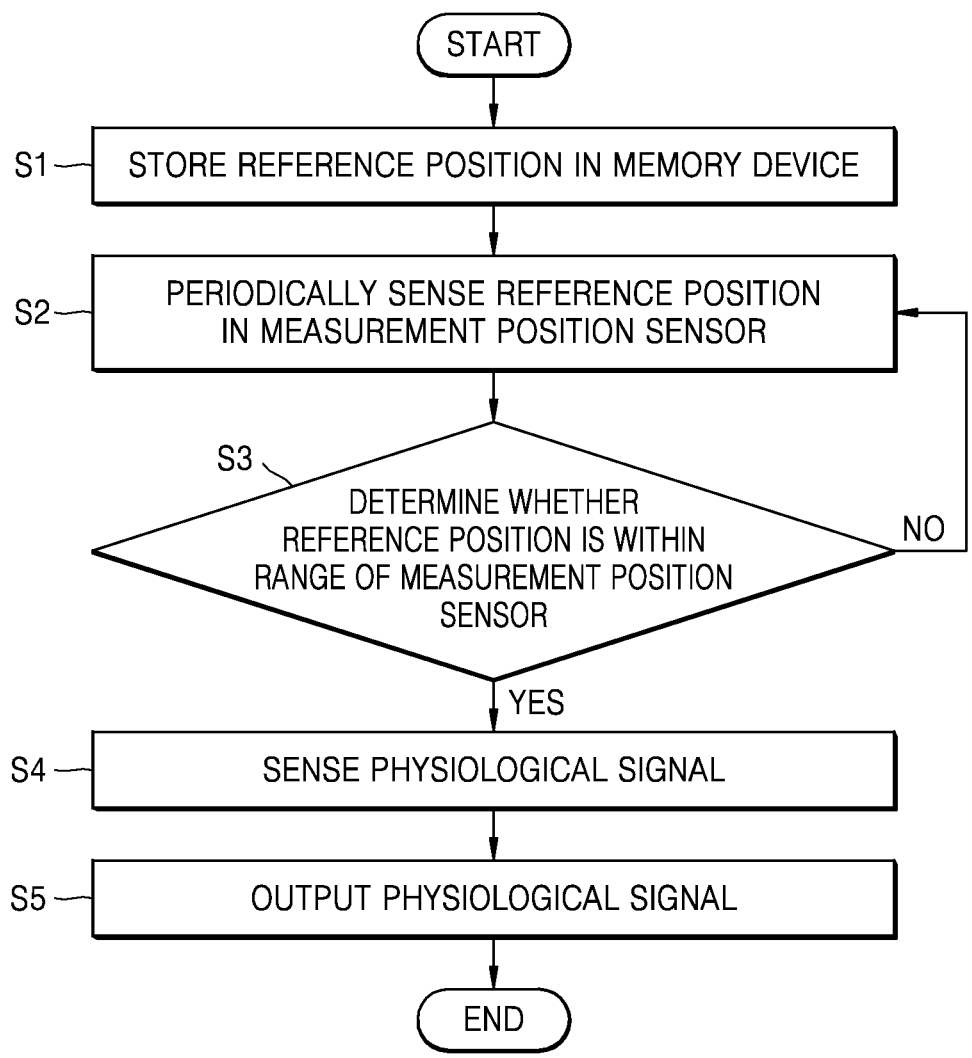
FIG. 2 illustrates a flowchart of a method for detecting a physiological or biometric signal by using the physiological signal analysis device according to an exemplary embodiment.

FIG. 2 is a flowchart illustrating a method for detecting a physiological or biometric signal by using the physiological signal analysis device according to an exemplary embodiment. Referring to FIG. 2, a wrinkle pattern and/or a wrinkle curve shape of a measurement body part (e.g., wrist skin) is recognized through the measurement position sensor 100, and is stored as the reference position 101 in the memory device 130 in operation S1. The wrinkle pattern and/or the wrinkle curve shape may be recognized using a fingerprint recognition technique, an optical mouse pattern recognition technique, or the like. Information recognized by the measurement position sensor 100 is not limited to a wrinkle shape and pattern, and may further include other micro features such as scars, freckles, and moles on the skin surface of the subject.

The measurement position sensor 100 periodically senses the reference position 101 in operation S2. The reference position 101 may be periodically sensed in various ways. For example, the reference position 101 may be periodically sensed, but not limited to, for 10 seconds every minute, for 10 seconds every 5 minutes, or for 10 seconds every 10 minutes.

Figure 3A:
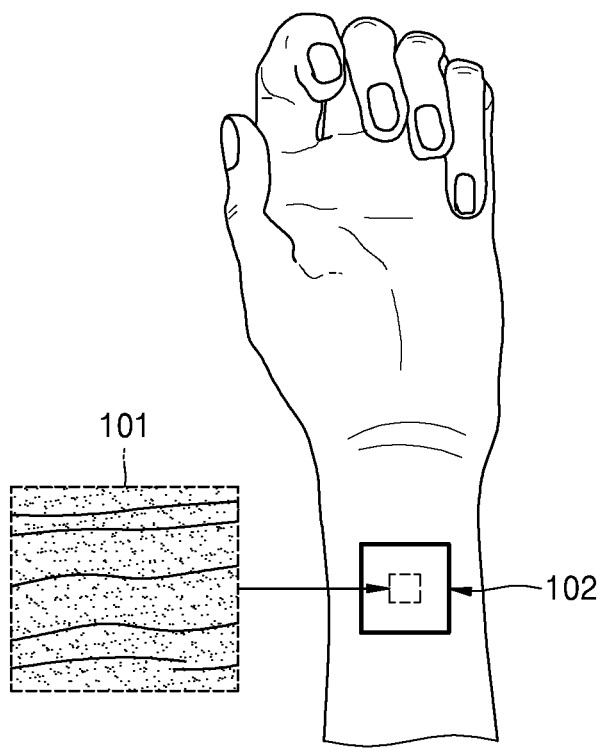
FIGS. 3A and 3B illustrate plan views showing a case where a reference position is in a range of a measurement position sensor in a physiological signal analysis device according to an exemplary embodiment.
Figure 3B:
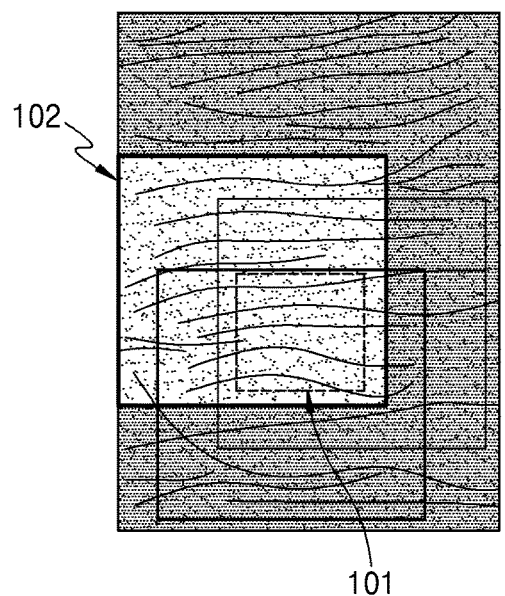
Figure 3C:
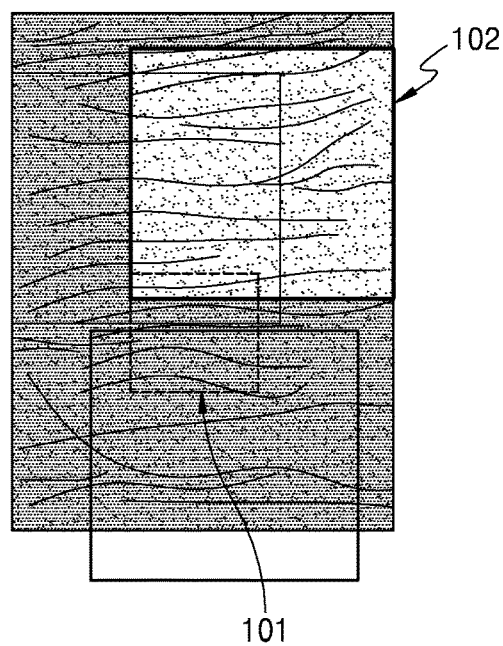
FIG. 3C illustrates a plan view showing a case where a reference position is out of a range of a measurement position sensor in a physiological signal analysis device according to an exemplary embodiment.

It is determined whether the reference position is in a range 102 of the measurement position sensor 100 in operation S3. For example, the signal processor 140 may recognize a set of wrinkles from an image as a curve pattern and find similarity between the recognized curve pattern and a reference curve pattern which is pre-stored in the memory device 130. Operation S3 will be further described with reference to FIGS. 3A, 3B, and 3C. FIGS. 3A and 3B are plan views corresponding to a case where the reference position 101 is in the range 102 of the measurement position sensor 100 in the physiological signal analysis device according to an exemplary embodiment, and FIG. 3C is a plan view corresponding to a case where the reference position 101 is out of the range 102 of the measurement position sensor 100 in the physiological signal analysis device according to an exemplary embodiment. If the reference position 101 is not in the range 102 of the measurement position sensor 100 as illustrated in FIG. 3C, the method returns to operation S2 in which the measurement position sensor 100 periodically senses the reference position 101.

On the other hand, if the reference position 101 is in the range 102 of the measurement position sensor 100 as illustrated in FIGS. 3A and 3B, the signal processor 140 performs signal processing to control the physiological signal sensor 110 to sense a physiological signal, in operation S4.

Next, the sensed physiological signal is displayed on the display 150 in operation S5. For example, the display 150 may be medical equipment using physiological information, a printer for printing a result, or a display device for displaying an analysis result. The display 150 may also be, but not limited to, a smart phone, a cellular phone, a personal digital assistant (PDA), a laptop, a personal computer (PC), and other mobile or non-mobile computing devices.

After operation S5, it may be further determined whether physiological signal detection has been completed; if physiological signal detection has not been completed, the method goes back to operation S2, and otherwise, if physiological signal detection has been completed, the method may be terminated.

A measurement position sensing pixel 103 or a physiological signal sensing pixel 111 may include at least one of a light emitter 112 for irradiating light to the subject, a light receiver 113 for receiving emitted light including a physiological signal from the subject, a capacitive electrode, an ultrasound wave generator for radiating an ultrasound wave to the subject, and an ultrasound wave receiver for measuring an emitted ultrasound wave including a physiological signal from the subject.

The measurement position sensing pixel 103 and the physiological signal sensing pixel 111 may have various positional relationships, as will be described with reference to FIGS. 4, 5, and 6.

Figure 4:
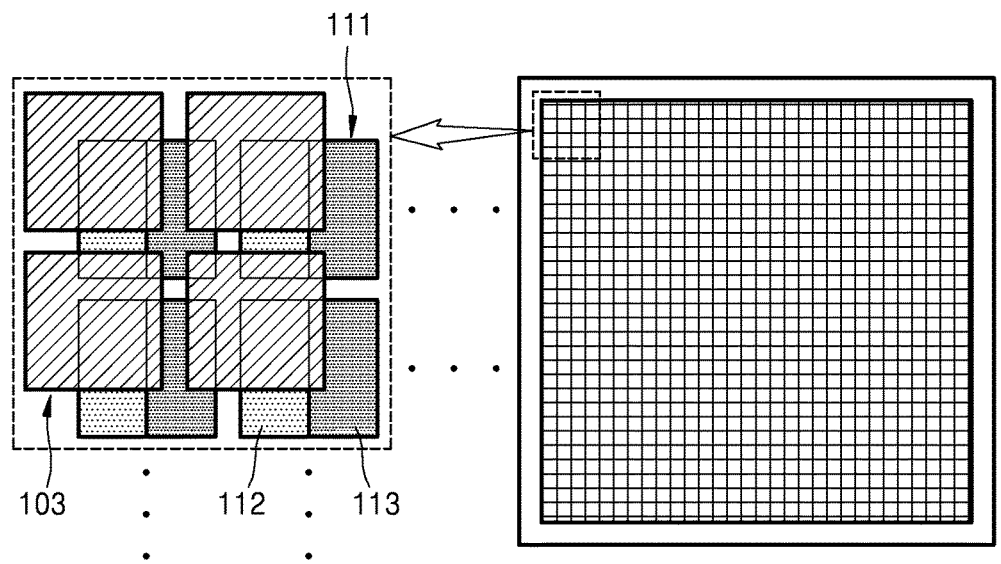
FIG. 4 illustrates a plan view of examples of a measurement position sensing pixel including a transparent electrode and a physiological signal sensing pixel including a light emitter and a light receiver in a physiological signal analysis device according to an exemplary embodiment.

FIG. 4 is a plan view showing examples of the measurement position sensing pixel 103 including a transparent electrode and the physiological signal sensing pixel 111 including a light emitter 112 and a light receiver 113 in the physiological signal analysis device according to an exemplary embodiment. Referring to FIG. 4, the measurement position sensing pixel 103 and the physiological signal sensing pixel 111 may overlap with each other when viewed in a vertical direction of a pixel surface. In this case, the measurement position sensing pixel 103 and the physiological signal sensing pixel 111 may be configured not to interfere with each other. For example, the measurement position sensing pixel 103 may include a transparent electrode for measuring a capacitance and the physiological signal sensing pixel 111 may include a light emitter 112 and a light receiver 113, so that the measurement position sensing pixel 103 may include a transparent electrode and the physiological signal sensing pixel 111 may not interfere with each other.

Figure 5:
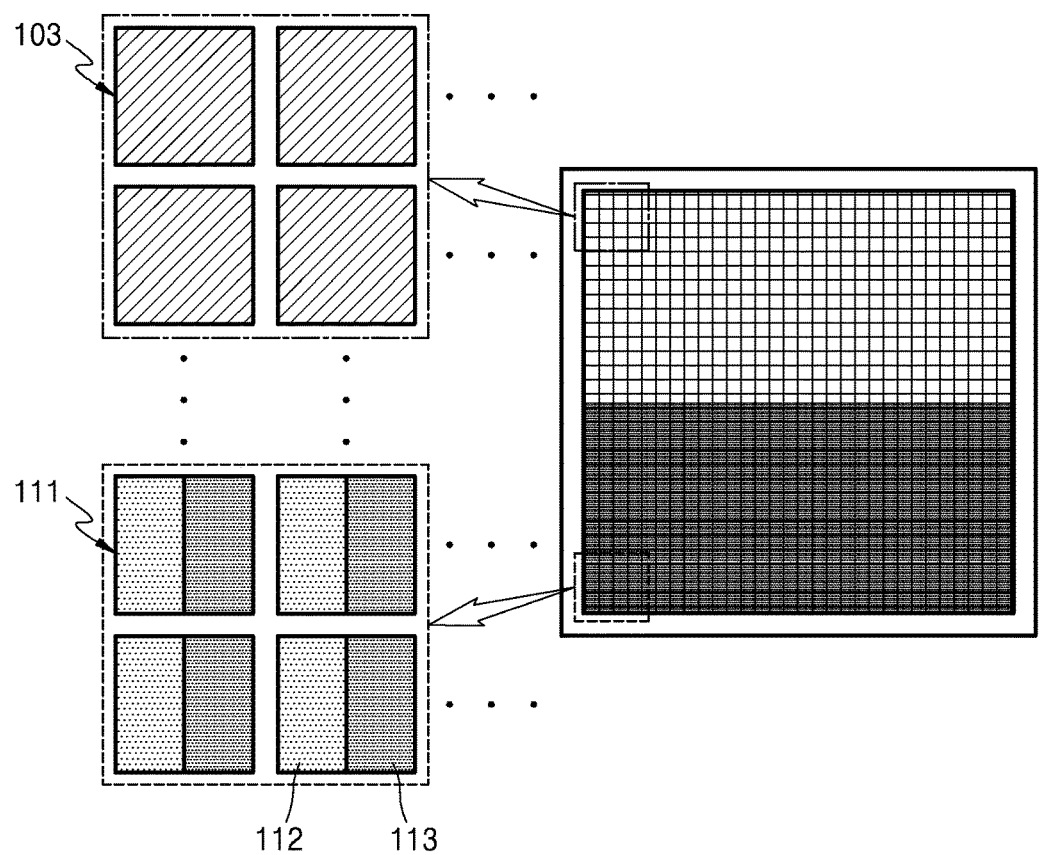
FIG. 5 illustrates a plan view of examples of a measurement position sensing pixel and a physiological signal sensing pixel that are separately configured on the same two-dimensional (2D) plane in a physiological signal analysis device according to an exemplary embodiment.

FIG. 5 is a plan view showing examples of the measurement position sensing pixel 103 and the physiological signal sensing pixel 111 that are separately configured on the same 2D plane in the physiological signal analysis device according to an exemplary embodiment. Referring to FIG. 5, the measurement position sensing pixel 103 and the physiological signal sensing pixel 111 may be separately configured on the same 2D plane. The physiological signal analysis device may not analyze a physiological signal at the reference position 101. Since the wrinkle shape and/or pattern at a measurement position is stored as the reference position 101 to sense a physiological signal at a consistent position, the physiological signal sensing pixel 111 corresponding to each measurement position sensing pixel 103 is set to obtain physiological information at the consistent position.

Figure 6:
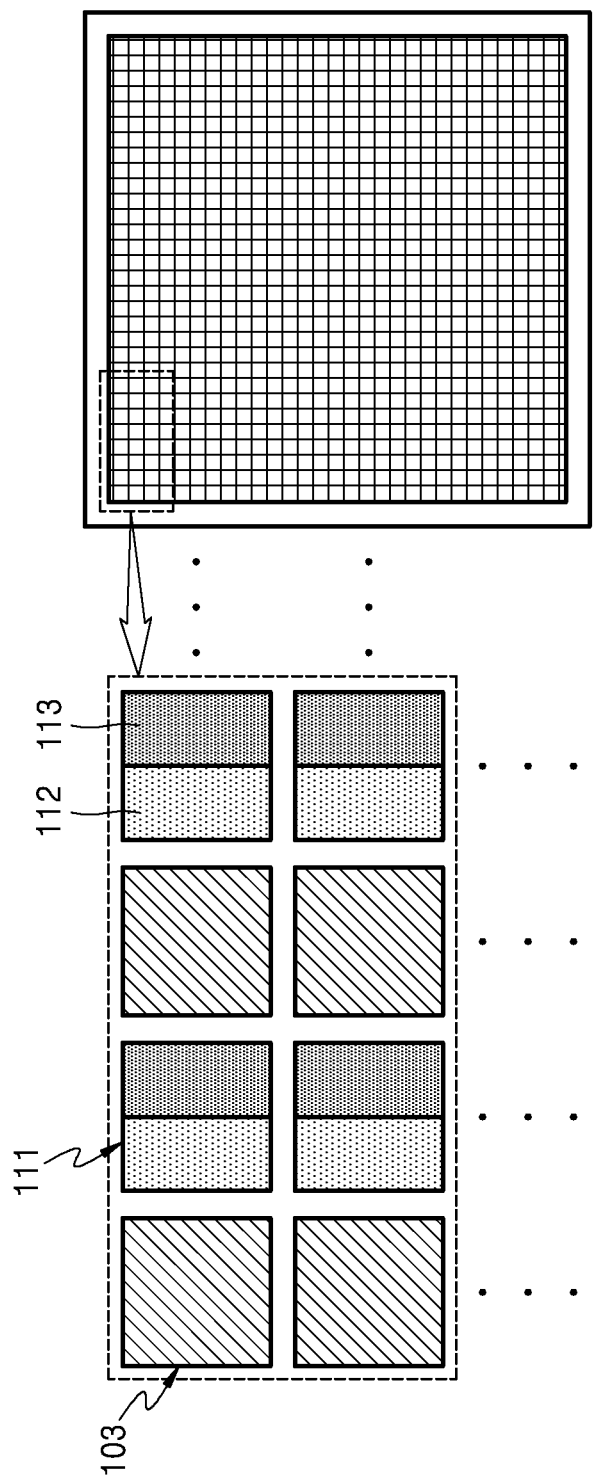
FIG. 6 illustrates a plan view of examples of a measurement position sensing pixel and a physiological signal sensing pixel that are arranged alternately on the same 2D plane in a physiological signal analysis device according to an exemplary embodiment.

FIG. 6 is a plan view showing examples of the measurement position sensing pixel 103 and the physiological signal sensing pixel 111 that are arranged alternately on the same 2D plane in the physiological signal analysis device according to an exemplary embodiment. The measurement position sensing pixel 103 and the physiological signal sensing pixel 111 may be arranged alternately. For example, the arrangement may be such that physiological signal sensing pixels 111 may be arranged on, under, to the left of, and to the right of one measurement position sensing pixel 103, and likewise, measurement position sensing pixels 103 may be arranged on, under, to the left of, and to the right of one physiological signal sensing pixels 111. Alternatively, as illustrated in FIG. 6, between the measurement position sensing pixels 103 arranged spaced apart from each other along one direction, the physiological signal sensing pixel 111 may be arranged along that direction.

The physiological signal analysis device may be modified in various embodiments, as will be described with reference to FIGS. 7 through 10.

Figure 7:
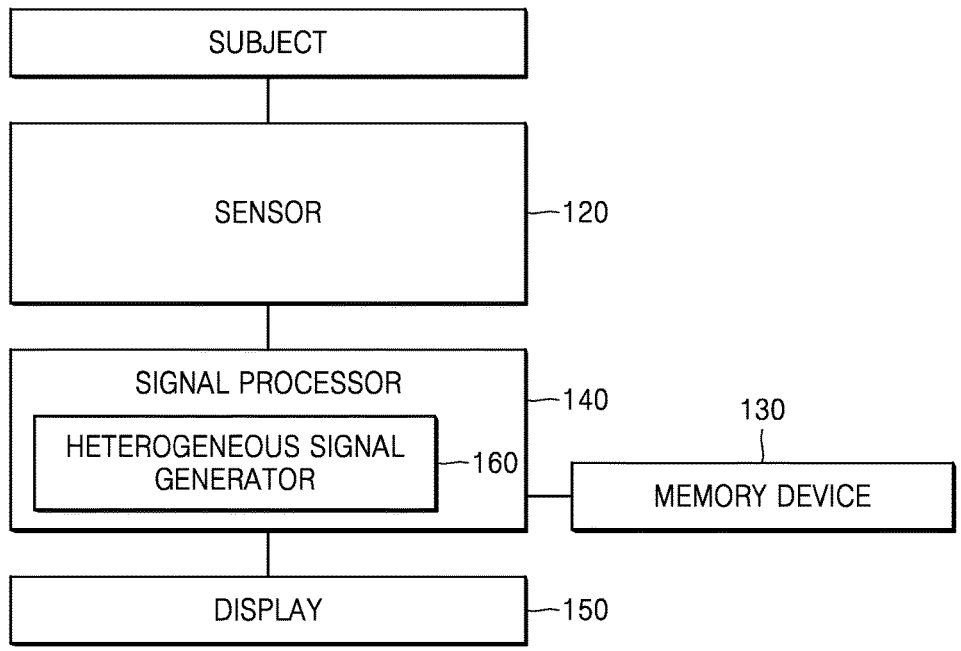
FIG. 7 illustrates a block diagram of the physiological signal analysis device illustrated in FIG. 1, in which a measurement position sensor and a physiological signal sensor are integrated and a heterogeneous signal generator is included in a signal processor.

FIG. 7 is a block diagram of a physiological signal analysis device illustrated in FIG. 1, in which the measurement position sensor 100 and the physiological signal sensor 110 are integrated into one sensor 120 and a heterogeneous signal generator 160 is included in the signal processor 140. Referring to FIG. 7, a measurement position sensing signal and a physiological signal sensing signal are separately generated according to heterogeneous driving signals generated by the heterogeneous signal generator 160 of the signal processor 140, and the sensor 120 differently senses the generated signals. For example, pixels of the sensor 120 may include a capacitive electrode, and a signal generated from the electrode may be classified into a measurement position sensing signal and a physiological signal sensing signal according to a frequency. In this case, the sensor 120 may include a single kind of pixels, simplifying manufacturing.

Figure 8:
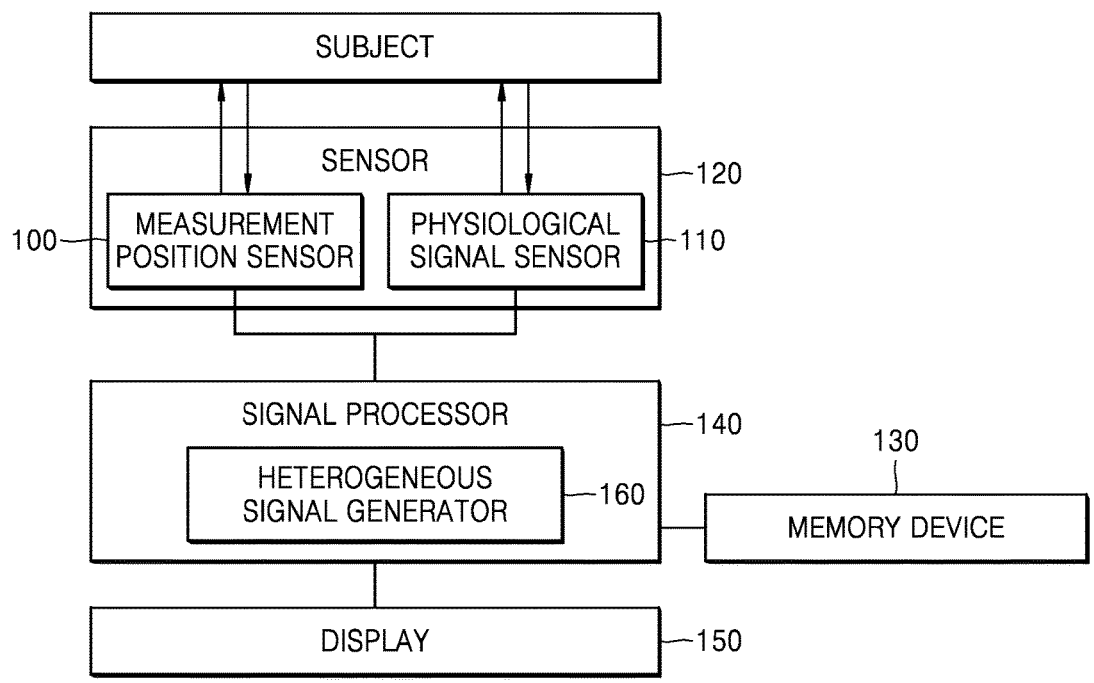
FIG. 8 illustrates a block diagram of the physiological signal analysis device illustrated in FIG. 1, in which a heterogeneous signal generator is included in a signal processor.

FIG. 8 is a block diagram of the physiological signal analysis device illustrated in FIG. 1, in which the heterogeneous signal generator 160 is included in the signal processor 140. Referring to FIG. 8, the sensor 120 may include the measurement position sensor 100 and the physiological signal sensor 110. The signal processor 140 may include the heterogeneous signal generator 160. A measurement position sensing signal and a physiological signal sensing signal are separately generated according to heterogeneous driving signals generated by the heterogeneous signal generator 160 of the signal processor 140. For example, once the measurement position sensing signal is generated by the heterogeneous signal generator 160, the measurement position sensor 100 may sense an electric-field signal, and if the physiological signal sensing signal is generated by the heterogeneous signal generator 160, the physiological signal sensor 110 senses an optical signal. In this case, various types of physiological signals are sensed for use in physiological signal analysis from various aspects.

Figure 9:
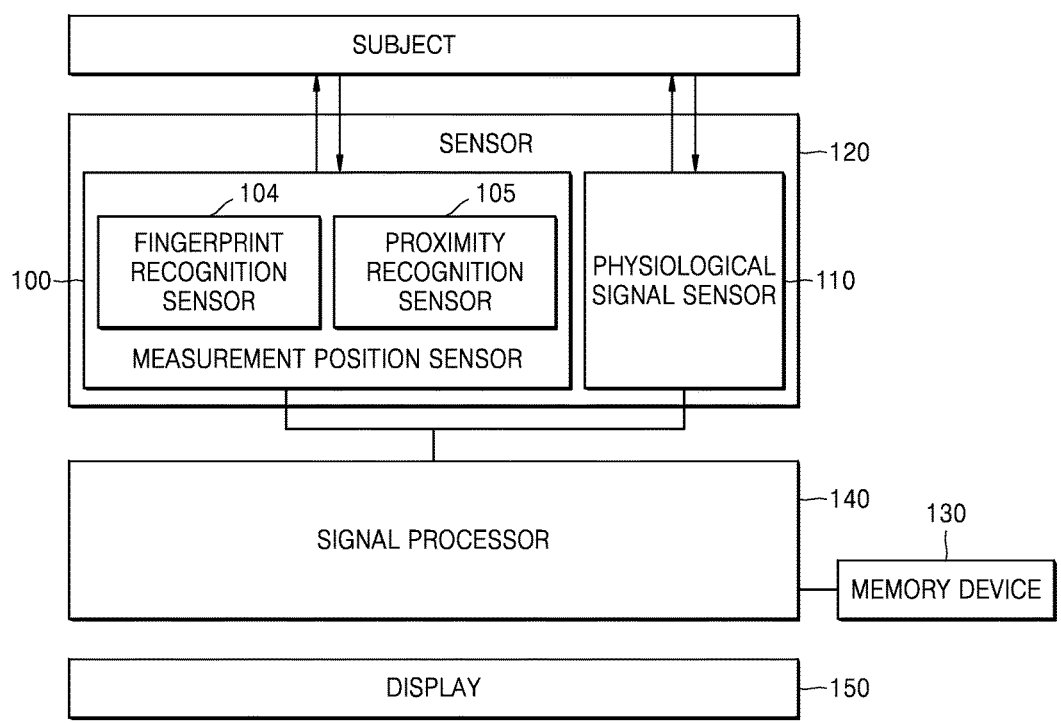
FIG. 9 illustrates a block diagram of the physiological signal analysis device illustrated in FIG. 1, in which a fingerprint recognition sensor and a proximity recognition sensor are included in a measurement position sensor.
Figure 10:
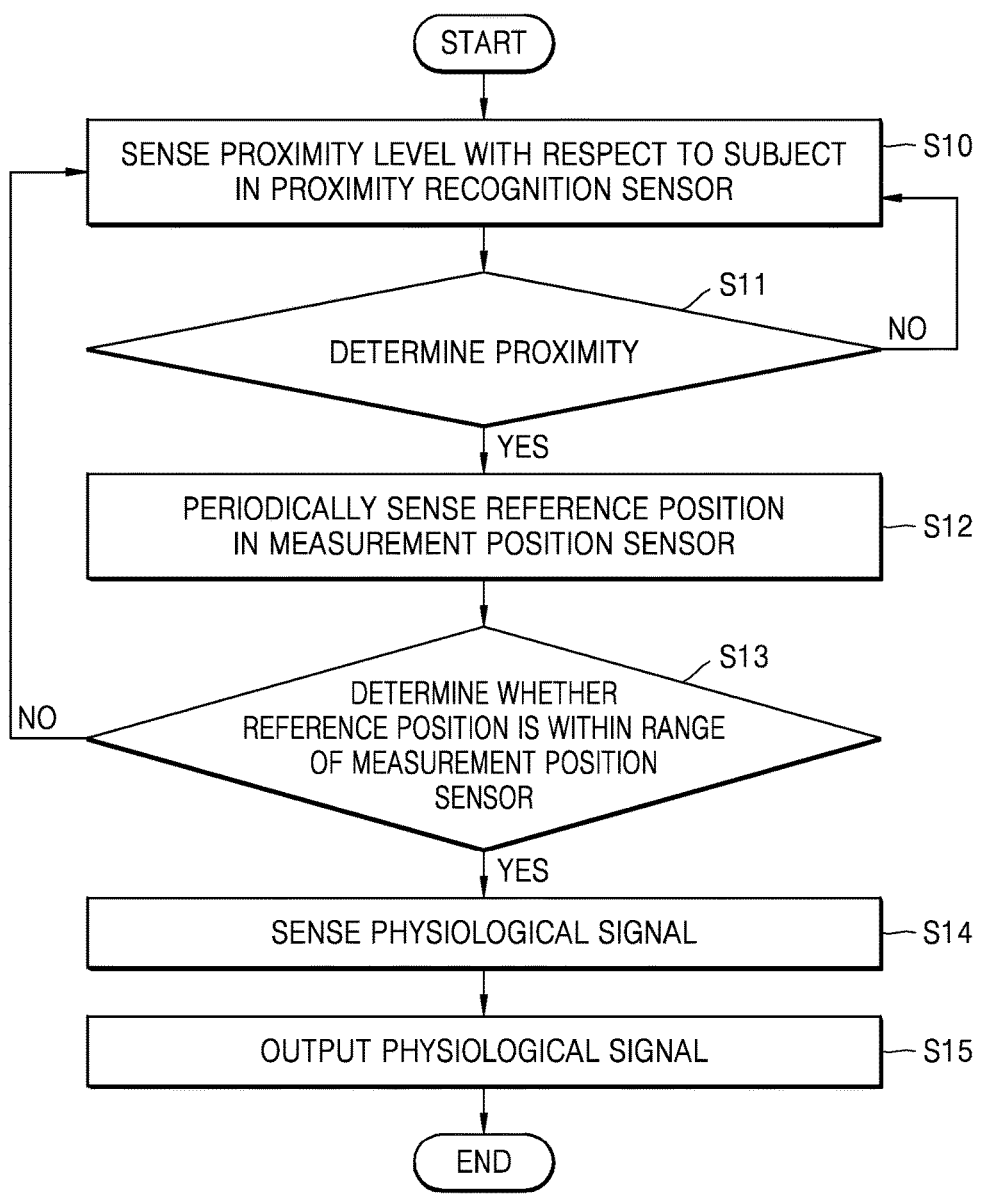
FIG. 10 illustrates a flowchart of a physiological signal detection method used by a physiological signal analysis device including a proximity recognition sensor according to an exemplary embodiment.

FIG. 9 is a block diagram of the physiological signal analysis device illustrated in FIG. 1, in which a fingerprint recognition sensor 104 and a proximity recognition sensor 105 are included in the measurement position sensor 100, and FIG. 10 is a flowchart illustrating a physiological signal detection method using the physiological signal analysis device including the proximity recognition sensor 105 according to an exemplary embodiment.

Referring to FIG. 9, when a measurement position is sensed, the proximity recognition sensor 105 identifies the reference position 101, considering a proximity corresponding to a distance between a body part and the sensor as a variable of the measurement position, thereby reducing the amount of computation in signal processing and thus achieving rapid data processing.

Referring to FIG. 10, the proximity recognition sensor 105 senses a proximity level with respect to a subject in operation S10.

Proximity to a measurement position is determined in operation S11. If the proximity recognition sensor 105 is not proximate to the measurement position, the method returns to operation S10.

On the other hand, if the proximity recognition sensor 105 is proximate to the measurement position, the measurement position sensor 100 periodically senses the reference position in operation S12. The reference position 101 may be periodically sensed in various ways. For example, the reference position 101 may be periodically sensed, but not limited to, for 10 seconds every minute, for 10 seconds every 5 minutes, or for 10 seconds every 10 minutes.

It is determined whether the reference position 101 is in the range 102 of the measurement position sensor 100 in operation S13. If the reference position 101 is not in the range 102 of the measurement position sensor 100 as illustrated in FIG. 3C, the method goes back to operation S10 in which the proximity recognition sensor 105 senses the proximity level with respect to the subject.

On the other hand, if the reference position 101 is in the range 102 of the measurement position sensor 100 as illustrated in FIGS. 3A and 3B, the signal processor 140 performs signal processing to control the physiological signal sensor 110 to sense the physiological signal, in operation S14.

The sensed physiological signal is displayed on the display 150 in operation S15. For example, the display 150 may be medical equipment using physiological information, a printer for printing a result, or a display device for displaying an analysis result. The display 150 may also be, but not limited to, a smart phone, a cellular phone, a PDA, a laptop, a PC, and other mobile or non-mobile computing devices.

The proximity recognition sensor 105 may also be provided as a plurality of proximity recognition sensors 105. If a single proximity recognition sensor 105 is provided, the fingerprint recognition sensor 104 may not contact the skin even if the proximity recognition sensor 105 contacts the skin. To avoid this situation, the plurality of proximity recognition sensors 105 are provided and perform fingerprint recognition sensing only when the fingerprint recognition sensor 104 contacts the skin.

In the physiological signal analysis device, the reference position 101 may be set in various ways, as will be described with reference to FIGS. 11 through 14.

Figure 11:
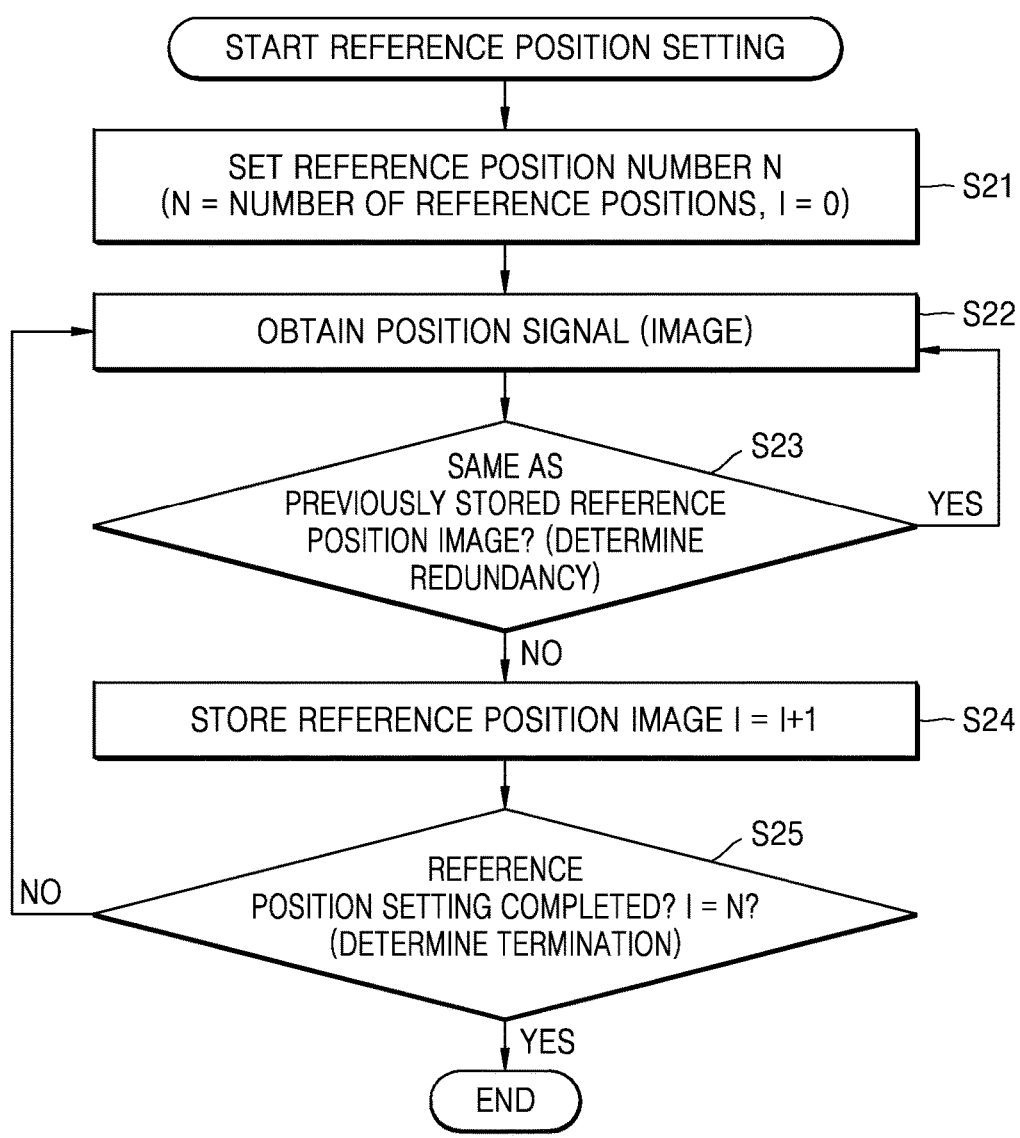
FIG. 11 illustrates a flowchart illustrating a method for automatically setting a single reference position or a plurality of reference positions in a physiological signal analysis device according to an exemplary embodiment.

FIG. 11 is a flowchart illustrating a method for automatically setting a single reference position or a plurality of reference positions in the physiological signal analysis device according to an exemplary embodiment. Referring to FIG. 11, the subject sets the number of reference positions 101, N, in operation S21. The number of reference positions may be greater than 1. The number of reference positions 101 is stored as N, and i is stored as 0.

The measurement position sensor 100 obtains a position signal in operation S22. The position signal may be an image of a wrinkle shape and/or a wrinkle pattern at a measurement body part of the subject.

It is determined whether the obtained position image is the same as a previously stored image of the reference position 101 in operation S23. If the obtained position image is the same as the previously stored image of the reference position 101, the method returns to operation S22.

On the other hand, if the obtained position image is different from the previously stored image of the reference position 101, the obtained position image is set and stored as a reference position, and i is stored as (i+1) in operation S24.

The value i is compared with the value N to determine whether setting of the reference position 101 has been completed in operation S25. If the value i is different from the value N, the method returns to operation S22; otherwise, if the value i is equal to the value N, setting of the reference position 101 is terminated.

Figure 12:
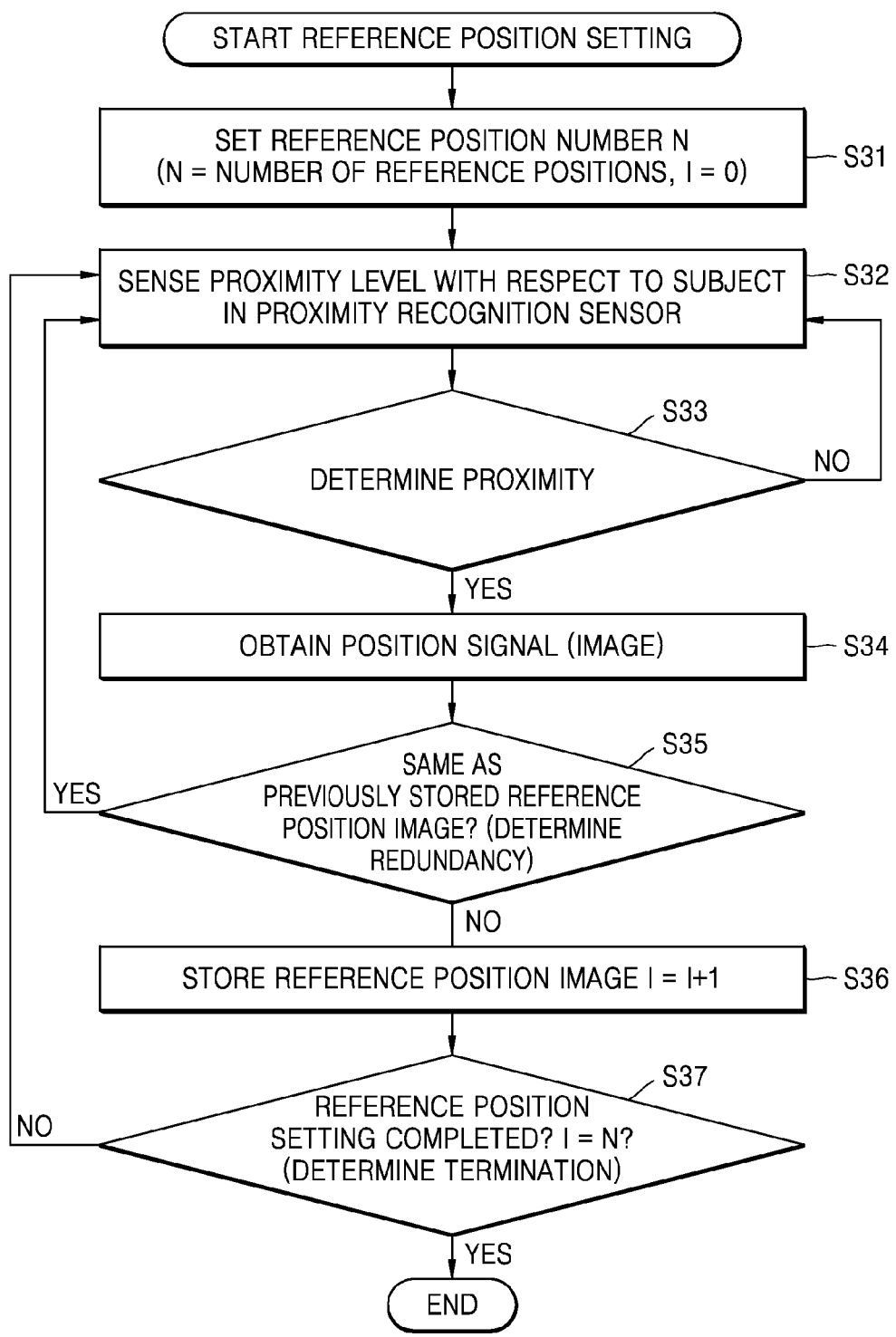
FIG. 12 illustrates a flowchart of a method for automatically setting a single reference position or a plurality of reference positions in a physiological signal analysis device including a proximity recognition sensor according to an exemplary embodiment.

FIG. 12 is a flowchart illustrating a method for automatically setting a single reference position or a plurality of reference positions in the physiological signal analysis device including the proximity recognition sensor 105 according to an exemplary embodiment. Referring to FIG. 12, the subject sets the number of reference positions 101 in operation S31. The number of reference positions may be greater than 1. The number of reference positions 101 is set as N and i is set as 0.

The proximity recognition sensor 105 senses a proximity level with respect to the subject in operation S32.

Proximity with the measurement position is determined in operation S33. If the proximity recognition sensor 105 is not proximate to the measurement position, the method returns to operation S32.

On the other hand, if the proximity recognition sensor 105 is proximate to the measurement position, the measurement position sensor 100 obtains a position signal in operation S34. The position signal may be an image of a wrinkle shape and/or a wrinkle pattern at the measurement body part of the subject.

It is determined whether the obtained position image is the same as a previously stored image of the reference position 101 in operation S35. If the obtained position image is the same as the previously stored image of the reference position 101, the method returns to operation S32.

On the other hand, if the obtained position image is different from the previously stored image of the reference position 101, the obtained position image is set and stored as a reference position, and i is stored as (i+1) in operation S36.

The value i is compared with the value N to determine whether setting of the reference position 101 has been completed in operation S37. If the value i is different from the value N, the method goes back to operation S32; otherwise, if the value i is equal to the value N, setting of the reference position 101 is terminated.

Figure 13:
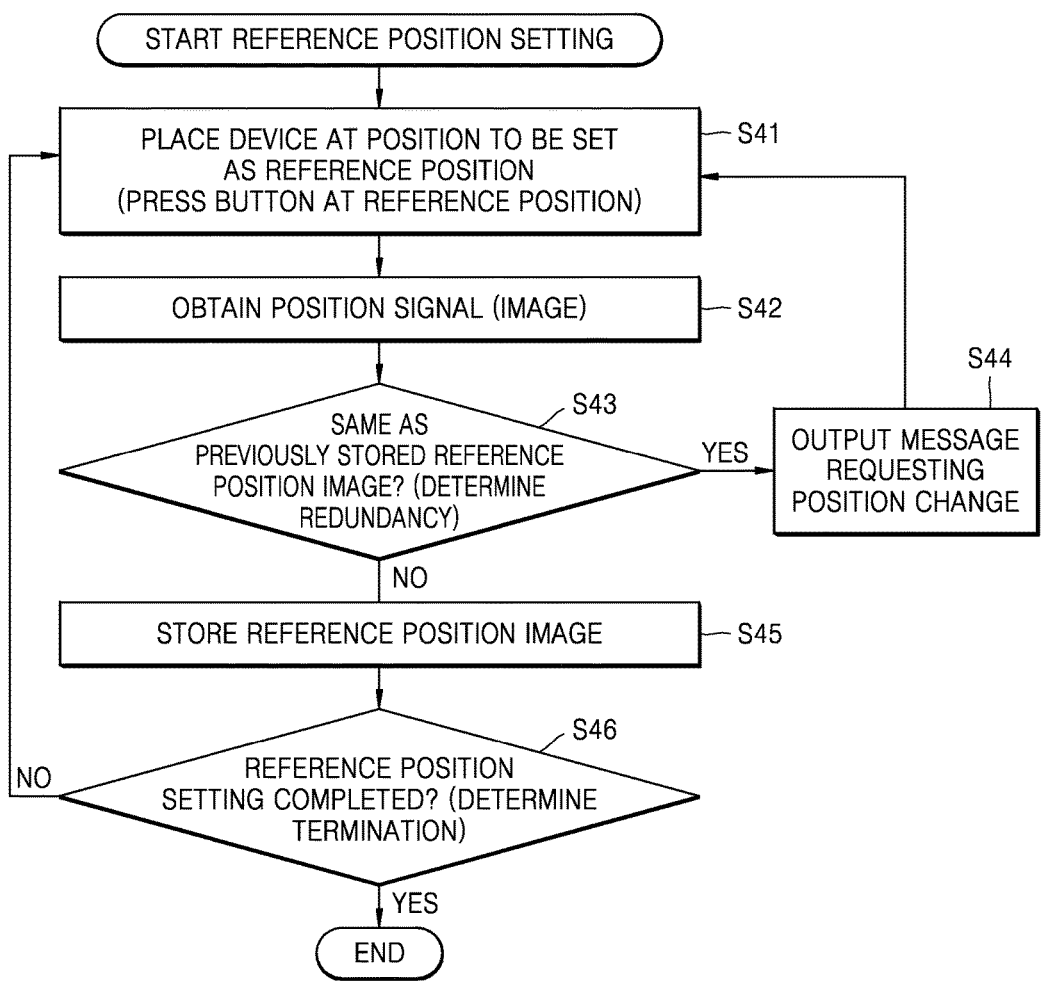
FIG. 13 illustrates a flowchart of a method for manually setting a single reference position or a plurality of reference positions in a physiological signal analysis device according to an exemplary embodiment.

FIG. 13 is a flowchart illustrating a method for manually setting a single reference position or a plurality of reference positions in the physiological signal analysis device according to an exemplary embodiment. Referring to FIG. 13, the physiological signal analysis device is placed at a position to be set as the reference position 101 in operation S41. This operation may be performed by placing the physiological signal analysis device at the position to be set as the reference position 101 and then pressing a button.

Next, the measurement position sensor 100 obtains a position signal in operation S42. The position signal may be a wrinkle shape image at the measurement body part of the subject.

It is determined whether the obtained position image is the same as a previously stored image of the reference position 101 in operation S43. If the obtained position image is the same as the previously stored image of the reference position 101, a message requesting position change is output in operation S44 and the method goes back to operation S41.

On the other hand, if the obtained position image is different from the previously stored image of the reference position 101, the obtained position image is set and stored as a reference position in operation S45.

It is determined whether setting of the reference position 101 has been completed in operation S46. If setting of the reference position 101 has not been completed, the method returns to operation S41; otherwise, if setting of the reference position has been completed, setting of the reference position 101 is terminated.

Figure 14:
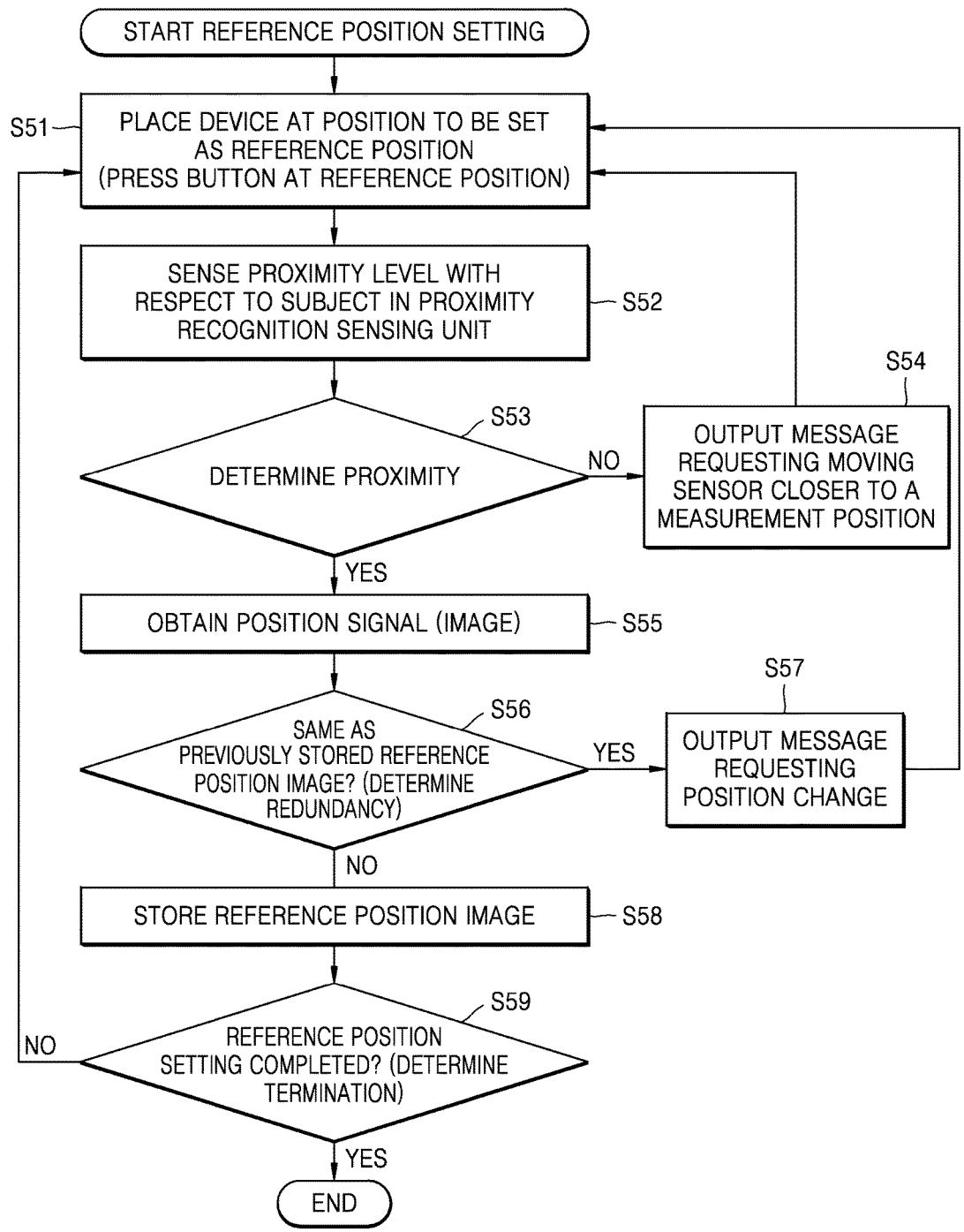
FIG. 14 illustrates a flowchart of a method for manually setting a single reference position or a plurality of reference positions in a physiological signal analysis device including a proximity recognition sensor according to an exemplary embodiment.

FIG. 14 is a flowchart illustrating a method for manually setting a single reference position or a plurality of reference positions in the physiological signal analysis device including the proximity recognition sensor 105 according to an exemplary embodiment. Referring to FIG. 14, the physiological signal analysis device is placed at a position to be set as the reference position 101 in operation S51. This operation may be performed by placing the physiological signal analysis device at the position to be set as the reference position 101 and then pressing a button.

The proximity recognition sensor 105 senses a proximity level with respect to the subject in operation S52.

Proximity with the measurement position is determined in operation S53. If the proximity recognition sensor 105 is not proximate to the measurement position, a message requesting moving the sensor closer to the measurement position is output in operation S54 and the method returns to operation S51.

On the other hand, if the proximity recognition sensor 105 is proximate to the measurement position, the measurement position sensor 100 obtains a position signal in operation S55. The position signal may be a wrinkle shape image at a measurement body part of the subject.

It is determined whether the obtained position image is the same as a previously stored image of the reference position 101 in operation S56. If the obtained position image is the same as the previously stored image of the reference position 101, a message requesting position change is output in operation S57, and the method returns to operation S51.

On the other hand, if the obtained position image is different from the previously stored image of the reference position 101, the obtained position image is set and stored as a reference position in operation S58.

It is determined whether setting of the reference position 101 has been completed in operation S59. If setting of the reference position 101 has not been completed, the method returns to operation S51; otherwise, if setting of the reference position 101 has been completed, setting of the reference position 101 is terminated.

As described above, according to the one or more of the above exemplary embodiments, physiological information at a consistent measurement position is collected, such that consistent and accurate physiological signal analysis may be performed.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While exemplary embodiments have been described with reference to the figures, it will be understood by those of ordinary skill in the art that various changes in form and details may be made therein without departing from the spirit and scope as defined by the following claims.

What is claimed is:

1. A physiological signal analysis device comprising:
 a memory configured to store a first wrinkle pattern at a reference position of a subject, as a reference position image;
 a fingerprint scanner comprising a measurement position sensing pixel to obtain a second wrinkle pattern at a measurement position, as a measurement position image;

a processor configured to determine whether the reference position is placed within a sensing area of the fingerprint scanner based on comparison between the first wrinkle pattern and the second wrinkle pattern; and
a physiological signal sensor comprising a physiological signal sensing pixel comprising a light emitter and a light receiver which are disposed underneath the fingerprint scanner to sense a physiological signal of the subject at the reference position in response to the reference position being determined to be placed within the sensing area of the fingerprint scanner,
wherein the processor is further configured to process the physiological signal,
wherein the measurement position sensing pixel of the fingerprint scanner is laid over the entire physiological signal sensor comprising the light emitter and the light receiver, so that the physiological signal sensor senses the physiological signal of the subject based on a light that is emitted to the subject through the fingerprint scanner and collected from the subject through the fingerprint scanner.

2. The physiological signal analysis device of claim 1, further comprising a display configured to display the physiological signal processed by the processor.

3. The physiological signal analysis device of claim 2, wherein the memory, the physiological signal sensor, the processor, and the display are connected to a wearable device worn by the subject, a healthcare related device, or a medical device.

4. The physiological signal analysis device of claim 3, further comprising:
a proximity recognition sensor configured to sense a contact state of the subject with respect to the reference position.

5. The physiological signal analysis device of claim 4, wherein the proximity recognition sensor comprises a plurality of proximity recognition sensors.

6. The physiological signal analysis device of claim 1,
wherein the measurement position sensing pixel of the fingerprint scanner overlaps with the light emitter and the light receiver of the physiological signal sensor in a vertical direction of a surface of the measurement position sensing pixel.

7. The physiological signal analysis device of claim 6, wherein the physiological signal sensing pixel further comprises:
an ultrasound wave generator configured to radiate an ultrasound wave to the subject; and
an ultrasound wave receiver configured to measure the ultrasound wave that is reflected from the subject and carries physiological information of the subject.

8. The physiological signal analysis device of claim 7, wherein the measurement position sensing pixel of the fingerprint scanner comprises a transparent electrode that prevents the measurement position sensing pixel of the fingerprint scanner and the physiological signal sensing pixel of the physiological signal sensor from interfering with each other.

9. The physiological signal analysis device of claim 6, wherein the processor comprises a heterogeneous signal generator configured to separately generate a measurement signal sensing signal and a physiological signal sensing signal according to heterogeneous driving signals for the fingerprint scanner and the physiological signal sensor, respectively.

10. The physiological signal analysis device of claim 9, wherein the measurement position sensing pixel is configured to sense an electric-field signal and the physiological signal sensing pixel is configured to sense an optical signal.

11. The physiological signal analysis device of claim 1, wherein the processor comprises a heterogeneous signal generator configured to separately generate a measurement signal sensing signal and a physiological signal sensing signal according to heterogeneous driving signals.

12. A physiological signal analysis method comprising:
setting and storing a first wrinkle pattern that is obtained at a reference position of a subject, as a reference position image;
obtaining, by a fingerprint scanner including a measurement position sensing pixel, a second wrinkle pattern at a measurement position, as a measurement position image,
determining whether the reference position is placed within a sensing area of the fingerprint scanner based on comparison between the first wrinkle pattern and the second wrinkle pattern;
measuring, by a physiological signal sensor including a physiological signal sensing pixel including a light emitter and a light receiver, a physiological signal at the reference position in response to the reference position being determined to be placed within the sensing area of the fingerprint scanner,
wherein the measuring the physiological signal comprises sensing the physiological signal of the subject based on a light that is emitted to the subject through the measurement position sensing pixel of the fingerprint scanner which is laid over the entire physiological signal sensor including the light emitter and the light receiver, and collected from the subject through the measurement position sensing pixel of the fingerprint scanner.

13. The physiological signal analysis method of claim 12, wherein the setting and storing of the first wrinkle pattern comprises automatically setting and storing a single reference position or a plurality of reference positions.

14. The physiological signal analysis method of claim 12, wherein the setting and storing of the first wrinkle pattern comprises determining, by a proximity recognition sensor, a proximity with respect to the measurement position, and setting and storing a single reference position or a plurality of reference positions in response to the proximity recognition sensor being proximate to the measurement position.

15. The physiological signal analysis method of claim 12, wherein the setting and storing of the first wrinkle pattern comprises manually setting and storing a single reference position or a plurality of reference positions.

16. The physiological signal analysis method of claim 12, wherein the setting and storing of the first wrinkle pattern comprises manually setting and storing a single reference position or a plurality of reference positions in response to determining that a proximity recognition sensor is proximate to the measurement position.

* * * * *